United States Patent [19]

Callanain

[11] Patent Number: 4,976,975
[45] Date of Patent: Dec. 11, 1990

[54] NOVEL MICROORGANISM AND USE THEREOF IN RIPENING CHEESE

[75] Inventor: Tadgh Callanain, Cheshire, United Kingdom

[73] Assignee: Agricultural Genetics Company Limited, England

[21] Appl. No.: 416,675

[22] Filed: Oct. 5, 1989

[30] Foreign Application Priority Data

Oct. 5, 1988 [GB] United Kingdom ............... 8823429

[51] Int. Cl.$^5$ .................. A23C 19/32; A23C 19/72
[52] U.S. Cl. ................................ 426/36; 426/40; 426/582
[58] Field of Search ............... 426/36, 38, 40, 582

[56] References Cited

U.S. PATENT DOCUMENTS

| | | | |
|---|---|---|---|
| 3,175,915 | 3/1965 | Murphy | 426/36 |
| 3,875,305 | 4/1975 | Storrs | 426/36 |
| 4,415,594 | 11/1983 | Czulak et al. | 426/36 |
| 4,588,593 | 5/1986 | Barthelemy et al. | 426/36 |

FOREIGN PATENT DOCUMENTS

| | | |
|---|---|---|
| 0150743 | 8/1985 | European Pat. Off. |
| 2606255 | 5/1988 | France . |
| 1250237 | 8/1986 | Switzerland . |

OTHER PUBLICATIONS

Arbige M. V. et al., Novel Lipases for Cheddar Cheese Flavour Development, *Food Technology*, 91–98, Apr. 1986.

Davies F. L. and Law B. A. (Editors), National Institute for Research in Dairying, Shinfield, Reading, U. K..

Grappin R. et al., Primary Proteolysis of Cheese Proteins During Ripening. *Journal of Dairy Science* 68, 531–540, 1985.

Law B. A., Accelerated Ripening of Cheddar Cheese with Microbial Proteinases. *Netherlands Milk and Dairy Journal* 35 (1981), pp. 313–327.

Lavery WO 82/03971 Published, Nov. 25, 1982.

Thomas, T. D., Oxidative Activity of Bacteria from Cheddar Cheese, *New Zealand Journal of Dairy Science and Technology* 21, 37–47, 1986.

Rank, T. C. et al., Secondary Proteolysis of Cheese During Ripening. *Journal of Dairy Science* 86, 801–805, 1985.

Pettersson et al., Chemical Abstracts, vol. 108, (21), p. 1854239q (Jun., 1988).

Bartels et al., Chemical Abstracts, Bol. 107 (7), p. 57630n (1987).

Girgis et al., Chemical Abstracts, vol. 100 (19), p. 15537Yg (1986).

Goraov, Chemical Abstracts, vol. 78 (11), p. 70370e (1973).

Hickey et al., Chemical Abstracts, vol. 100, p. 4985f, (1983).

El Soda et al., "Use of Enzymes in Food Technology," International Symposium, Versailles 5–7, May 1982, Lavoisier, Paris, France, 1982, pp. 299–302.

*Primary Examiner*—Marianne Cintins
*Attorney, Agent, or Firm*—Lowe, Price, LeBlanc, Becker & Shur

[57] ABSTRACT

The invention relates to *Lactobacillus helveticus* AGCl, a sample of which has been deposited on 29 September 1988 at The National Collections of Industrial And Marine Bacteria Limited under the accession number NCIB 40051, or a mutant or derivative thereof. This strain is useful as part of a starter culture addition to cheese milk, for accelerated ripening of cheddar style cheeses.

7 Claims, No Drawings

NOVEL MICROORGANISM AND USE THEREOF IN RIPENING CHEESE

This invention relates to a novel microorganism and its use in a method for the accelerated ripening of hard type cheeses of the Cheddar and related variant types, including low fat cheddar style cheese.

After initial manufacture, Cheddar cheese and Cheddar style varieties of cheese require a storage period of the order of four to six months at about 7° C., prior to sale. This storage period is necessary to allow the body of the cheese to acquire the typical characteristics of Cheddar cheese in terms of texture, consistency, and flavour. This extended storage period has evident disadvantages with respect to the financing costs of the cheese stocks involved, and with respect to marketing and production planning.

The development of typical Cheddar cheese, body, texture and flavour is the end result of complex physical and biochemical processes. These processes are influenced by a wide range of factors such as the composition and bacterial flora of the raw milk, the hygienic and manufacturing conditions used, the type of and condition of the starter bacteria used and the type of adventitious organisms present in the finished cheese. The composition of the cheese produced, the length of ripening period, and the temperature of storage during the ripening period are also important with respect to the development of a typical Cheddar cheese texture and flavour.

It is recognized that the body of the cheese is mainly modified from the initial 'curdy' texture and appearance of freshly produced cheddar cheese to that of a typical cheese as purchased by the consumer, by the proteolytic action of retained chymosin, by the proteolytic and peptidase enzymes, produced by the lactic acid starter bacteria and by adventitious organisms. These adventitious non-starter bacteria form the major flora of cheddar cheese after a relatively short period of ripening. The influence and interrelationships of these factors, in terms of cheese flavour and cheese texture, are as yet relatively undefined.

Manufacture of low fat cheeses presents problems in that flavour development is extremely slow and consequently such cheeses have a low consumer appeal.

A number of attempts to accelerate the flavour development of Cheddar and low fat Cheddar-style cheeses have been described.

EP-A-No. 0150743 describes a method for accelerating the aging process of Cheddar style cheese which is based on the use of preserved, partially disrupted preparation of the lactic acid bacterium *Lactobacillus caesi, Lactobacillus lactis, Lactobacillus olantarum* and a blend of pre-gastric lipases.

WO No. 82/03971 describes a method for the production of a low fat cheese product with enhanced flavour, using a culture of *Lactobacillus bulgaricus* and *Streptococcus thermophilus* and with a culture of *Lactobacillus caesi,* in addition to a normal cheese starter.

A number of methods to achieve accelerated ripening of Cheddar style cheeses, mainly based on enzyme additions are now commercially available or publicized (refs: 1,4,5,6).

However, one of the disadvantages of some of the systems is that the enzyme preparation has to be added to the cheese curd during the salt addition process and can give rise to enzyme distribution problems in the finished cheese, potentially resulting in flavour variations and physical defects such as cheese mottling. In the United Kingdom these systems have an additional disadvantage in that enzyme additions, other than coagulating enzymes, are not permitted under current cheese regulations, in traditional English type cheeses manufactured for direct sale to the consumer.

EP-A-No. 0150743 suffers from the disadvantage that cells of the lactic acid bacteria must be partially disrupted and then preserved before use. Such a process is technically difficult to operate and adds to the cost of cheese manufacture. WO No. 82/03971 suffers from the disadvantage that three cultures, in addition to a normal cheese starter, must be used.

The present invention relates to the surprising discovery that addition of a specific culture of *Lactobacillus helveticus* AGC1, characterized by its carbohydrate utilization pattern, and by its content of the nucleotides, guanine and cytosine (38.5%), to a typical manufacturing process for Cheddar and low fat Cheddar-style cheeses results in accelerated ripening.

The invention thus provides *Lactobacillus helveticus* AGC1, a sample of which has been deposited on 29 Sept. 1988 at The National Collections of Industrial and Marine Bacteria Ltd (NCIMB), P.O. Box 31, 135 Abbey Road, Aberdeen AB9 8DG, UK, under accession number NC1B 40051, or a mutant or derivative thereof.

*L. helveticus* AGC1 can be distinguished from other strains of *L. helveticus* by its characteristic carbohydrate utilization pattern (see Table 1). Thus, the invention provides a novel strain of *L. helveticus* which can be used to accelerate ripening of Cheddar style cheeses.

In practice, the additional culture is added at the normal point of starter culture addition to cheese milk, during the cheese making process. The rate of culture addition can be varied as required and is normally in the range of 0.01–1% and preferably 0.05% to 0.3%.

The addition of *L. helveticus* AGC1 in this manner may be regarded as the deliberate addition of a non-traditional (in this application) lactic acid starter bacterium, as a source of additional peptidases and proteolytic enzymes. This method produces the correct amount and type of breakdown in the body of the cheese, as determined by an expert cheese grader, and confirmed rheologically by means of measurements using an Instron universal tester instrument.

Novel aspects of our invention include the following:

1. A method for producing Cheddar cheese or Cheddar-like cheeses of composition in the range of 20–38% fat content and 30–45% moisture content made in a usual Cheddar cheese manufacturing type operation, with the specific addition of the identified strain of *Lactobacillus helveticus* AGC1 in addition to the usual cheese starter culture organisms. Such a method results in a cheese characterized by an accelerated ripening profile and in which unacceptable changes in texture do not occur.

2. A method for the production of a low fat Cheddar style cheese with a fat content in the range 8–20% and a moisture content in the range of 37–54% made with the specified strain of *Lactobacillus helveticus* AGC1, in addition to the usual cheese starter culture organisms. Such a method results in a cheese characterized by an accelerated ripening profile and in which unacceptable changes in texture do not occur.

*L. helveticus* AGC1 is a thermophilic strain and has an optimum temperature for growth that is higher than that of normal starter cultures. For that reason it is important that the scald temperature is maintained in the range of 95°–108° F. (35°–42.2° C.). Within this temperature range growth of all the starter cultures is maintained in balance. At higher temperatures *L. helveticus* AGC1 will overrun traditional cultures resulting in a poor quality cheese.

The application of the invention is exemplified in the following Examples.

EXAMPLE 1

Typical Cheddar Cheese Manufacturing Schedule, with the addition of *Lactobacillus helveticus* AGC1

Raw Materials

A. Milk which should be clean fresh and free from off flavour, antibiotics or any other inhibitory substance and be of good bacteriological quality.
B. Starters—lactic cultures
 (i) Normal *S. lactis/S. cremoris* type. and
 (ii) *L. helveticus* AGC1
C. Rennet: Standard rennet, as necessary.
D. Anatto: Coloured variety only.
E. Salt: Standard cheese salt.

PROCESSING CONDITIONS

A Blend of normal starter cultures and the *L. helveticus* AGC1 culture, depending on the activity of the cultures and the type of acid profile required, is added at the rate of 0.5–2%. The L. *helveticus* AGC1 culture is added at the rate of 0.05–1%. Both cultures are added simultaneously at the beginning of the usual milk 'ripening' period, immediately prior to renneting. The scald temperature should be sufficiently high to promote growth of the *L. helveticus* AGC1 culture (i.e. in the range of 95°–108° F. (35°–42.2° C.). Temperatures outside this range may result in an excessive outgrowth of the *L. helveticus* ACG1 culture. No significant difference from control cheese should be noted in the rennet to mill time.

Salt addition must be targeted to give a salt level in the finished cheese of 1.6–1.8%. The uniformity of salt distribution is of prime importance. The culture will be inhibited by a high salt concentration, thereby nullifying the effect of accelerated ripening. The cheese is thereafter pressed and transferred to storage as per routine procedures.

Typical results are shown as compared to the control cheese, in Table 2, demonstrating the initial rapid textural change in cheese produced by the method of this application, as compared to the control sample. This process also results in the production of the appropriate level and type of proteinases and peptidases which, with the retained chysmosin, are responsible for the breakdown of the initial cheese body and the production of a typical body texture and flavour profile, or the precursor chemicals to produce characteristic Cheddar cheese flavour, body and texture.

One of the traditional flavour defects in Cheddar cheese is a "bitter" flavour, which is thought to be due to the production of hydrophobic peptides due to insufficient hydrolysis of the peptide chains. Our process appears to result in the rapid breakdown of peptides, in excess of that encountered in a control sample, with the production of greater amounts of single amino-acids, without the production of bitter 'off' flavours. An amino acid analysis of trichloroacetic acid (TCA) extracts of Control and Accelerated cheeses at various time intervals is given in Table 3.

We believe that the mode of action of the *L. helveticus* ACG1 culture is effectively the production of proteolytic and peptidase enzymes of the right quantity, type and character resulting in rapid breakdown of the protein structure to give the required texture, accompanied by extensive peptide hydrolysis, resulting in the production of a correct blend of amino acids, peptides, lipases, fatty acids, etc. which act as either the main flavour ingredient in cheese or the precursor for such flavour development. Our process produces a cheese which is ready for pre-packing or sale to consumer or customers in approximately 8 to 10 weeks, as shown in Table 2, as compared to sixteen to twenty weeks for cheese produced using standard techniques.

A typical comparison of the aging process for an accelerated Cheddar cheese, as compared to a control Cheddar cheese, is given in Table 2. In addition, surprisingly, we have noted that whereas flavour development continues at an accelerated rate, the texture changes in cheese produced by our method effectively reach a plateau for an indefinite period. In other words, once the initial texture changes are completed, evident, continuing unacceptable changes in texture do not occur, thus avoiding the production of an unacceptable product at any point in the life of the cheese.

EXAMPLE 2

Production of Low Fat Hard Type Cheese

To produce low fat cheese using *L. helveticus* ACG1, particular attention needs to be given to certain key areas:
Standardization of the cheese milk and its heat treatment.
The blending and addition of the lactic cultures.
Setting and cutting of the curd.
Scalding, stirring and pitching the curd.
Curd treatment or cheddaring.
Salting.
Pressing.
Fresh raw milk needs to be standardized, by the addition of skim milk or by partial separation to a given fat percentage, or fat to protein ratio.
The fat levels will depend upon:
1. Fat required in the end product.
2. Fat lost in the whey, or conversely, fat retained in the cheese.
3. Protein retained in the cheese.

For most factory conditions, the fat in the cheese will probably be less than 17% fat, therefore a fat to protein ratio of the order of 1:2, is required.

The fat reduced milk is pasteurized at 161°–162° F. (71.7°–72.2° C.) and cooled to 88° F. (31.1° C.) for incubation.

A blend of cultures is added to the vat milk and this consists of the normal cultures of the day and *L. helveticus* ACG1. The amount of culture and the ratio between cultures is governed by:
1. Acid development required to give the correct Rennet to Mill time (normally 3 hours 20 minutes to 3 hours 40 minutes).
2. Rate of maturation required.

At ripening temperature of 88° F. (31.1° C.) significant acidity development from the *L. helveticus* AGC1 cultures is not expected, or encountered. Too high ripening temperatures will result in the *L. helveticus* AGC1 culture outgrowing the normal culture, and over maturation of the resulting cheese.

Starter addition mix needs to be in the order of 1-2% and the *L. helveticus* AGC1 being added at 5-15% of the total inoculum. The length of ripening influences the moisture retaining properties of the curd and at least 35-45 minutes is required. Acidity at the end of the period is normally in the range 0.16-0.19% lactic acid.

At the end of ripening, standard rennet is added at the rate of 40 oz per 1000 gallons (0.249 g/l) of cheese milk.

The cheese milk is allowed to settle for approximately 45 minutes, or until the curd is firm. The exact cutting operation will vary from plant to plant, but the aim is to cut the curd fairly large, so as to retain as much moisture as possible. The stirring of the curd should be as gentle as possible, but obviously sufficient to prevent the curd matting at the bottom of the vat.

Scald temperatures ranging from 94°-96° F. (34.4°-35.6° C.) are used. The curd is milled with a Cheddar chip mill at an acidity of 0.55% lactic acid.

Salt addition is targeted to give approximately 1.4-1.5% salt in the finished cheese. Under salting may result in rapid proteolysis with bitter off flavour, whereas over salting will give cheese of poor texture and sweeter flavours. The cheese is pressed following standard cheese pressing procedures.

Typical recipes for production of conventional low fat Cheddar cheeses and for production of low fat Cheddar cheeses using *L. helveticus* AGC1 are given in Table 4. A typical comparison of the aging process for an accelerated low fat Cheddar cheese, as compared to a conventional low fat Cheddar cheese, is given in Table 5. Cheese produced by our method develops a mature flavour by 7 weeks whereas conventional low fat cheese does not reach this level of flavour development unless stored for unrealistic periods (i.e. greater than 18 weeks). In addition, surprisingly, low fat cheeses produced by our method do not undergo any unacceptable changes in texture.

REFERENCES

1. ARBIGE M.V. et al, Novel Lipases for Cheddar Cheese Flavour Development *Food Technology* 91-98, April 1986
2. DAVIS F. L. AND LAW B. L. (Editors), Advances in the Microbiology and Biochemistry of Cheese and Fermented Milks. Elsevier Applied Science Publishers. Pages 209-227
3. GRAPPIN R. et al, Primary Proteolysis of Cheese Proteins during Ripening. A Review. *Journal of Dairy Science* 68, 531-540, 1985.
4. LAW B. A., Accelerated Ripening of Cheddar Cheese with Microbial Proteinases. *Netherlands Milk and Dairy Journal* 35 (3), 313-327, 1981.
5. LAVERY AND SON PROPRIETARY LTD. WO No. 82/03971
6. MILES LABORATORIES, INC. EP-A-No. 0150 743
7. THOMAS, T. D., Oxidate Activity of Bacteria from Cheddar Cheese. *New Zealand Journal of Dairy Science and Technology* 21, 37-47, 1986.
8. RANK, T. C. et al, Secondary Proteolysis of Cheese During Ripening. *Journal of Dairy Science* 68, 801-805, 1985.

| | Fermentation Activity ** (3 = high, 2 = medium, 1 = low, 0 = negative) | | | | | | | | | |
|---|---|---|---|---|---|---|---|---|---|---|
| Carbon Source | AGC1 | NCDO H3 | NCDO H6 | NCDO H13 | NCDO H17 | NCDO 28 | NCDO 30 | ATCC 39538 | ATCC 39539 | ATCC* 39542 |
| Glucose | 3 | 3 | 3 | 3 | 3 | 3 | 3 | 3 | 3 | — |
| mannose | 3 | 3 | 3 | 3 | 3 | 3 | 3 | 3 | 3 | — |
| lactose | 3 | 3 | 3 | 3 | 3 | 1 | 3 | 1 | 3 | — |
| galactose | 3 | 0 | 1 | 3 | 3 | 1 | 3 | 0 | 3 | — |
| fructose | 3 | 2 | 2 | 1 | 1 | 1 | 2 | 3 | 3 | — |
| n-acetyl glucosamine | 1 | 0 | 0 | 3 | 0 | 1 | 3 | 3 | 3 | — |
| ribose | 0 | 0 | 0 | 0 | 0 | 0 | 0 | 0 | 3 | — |
| trehalose | 0 | 0 | 0 | 3 | 0 | 0 | 0 | 3 | 3 | — |
| maltose | 0 | 0 | 0 | 0 | 0 | 0 | 0 | 1 | 0 | — |
| sucrose | 0 | 0 | 0 | 0 | 0 | 0 | 0 | 3 | 3 | — |
| adonitol | 0 | 0 | 0 | 0 | 0 | 0 | 0 | 0 | 1 | — |
| mannitol | 0 | 0 | 0 | 0 | 0 | 0 | 0 | 0 | 3 | — |
| sorbitol | 0 | 0 | 0 | 0 | 0 | 0 | 0 | 0 | 2 | — |
| inulin | 0 | 0 | 0 | 0 | 0 | 0 | 0 | 0 | 3 | — |
| turanose | 0 | 0 | 0 | 0 | 0 | 0 | 0 | 0 | 3 | — |
| lyxose | 0 | 0 | 0 | 0 | 0 | 0 | 0 | 0 | 3 | — |
| sorbose | ALL TESTS NEGATIVE | | | | | | | | | |
| rhamnose | | | | | | | | | | |
| methyl-glucoside | | | | | | | | | | |
| amygdalin | | | | | | | | | | |
| arbutin | | | | | | | | | | |
| esculin | | | | | | | | | | |
| cellobiose | | | | | | | | | | |
| melibiose | | | | | | | | | | |
| melezitose | | | | | | | | | | |
| raffinose | | | | | | | | | | |
| starch | | | | | | | | | | |
| xylitol | | | | | | | | | | |
| gentiobiose | | | | | | | | | | |
| tagatose | | | | | | | | | | |
| fucose | | | | | | | | | | |
| arabitol | | | | | | | | | | |
| gluconate | | | | | | | | | | |

-continued

| Carbon Source | AGC1 | NCDO H3 | NCDO H6 | NCDO H13 | NCDO H17 | NCDO 28 | NCDO 30 | ATCC 39538 | ATCC 39539 | ATCC* 39542 |
|---|---|---|---|---|---|---|---|---|---|---|
| | | | | Fermentation Activity ** | | | | | | |
| | | | | (3 = high, 2 = medium, 1 = low, 0 = negative) | | | | | | |
| keto-gluconate | | | | | | | | | | |

*Morphologically dissimilar from LB1
— Not tested
**Based on readings 24h after incubation at 37° cC.
NCDO type cultures were all *L. helveticus* strains
ATCC 39538 was *L. lactis* strain
ATCC 39539 was *L. casei* strain
ATCC 39542 was *L. plantarum* strain

TABLE 2

TYPICAL AGEING PROFILE FOR ACCELERATED AS COMPARED TO CONVENTIONAL CHEDDAR CHEESE

| AGE OF CHEESE | GRADING/COMMENTS | |
|---|---|---|
| | VAT 9 (CONTROL) | VAT 10 (ACCELERATED) |
| 3 weeks | Typical young curd Insipid | Good body and texture similar to 8-9 week cheese |
| 7 weeks | Good body - texture Mild | Good body and texture, breaking down very nicely similar to 4-5 month Cheddar |
| 9 weeks | Good body - texture Mild | Good body and texture, on par with 5-6 month Cheddar |
| 10 weeks | Good body - texture Mild | Similar to a good 5-6 month Cheddar |
| 12 weeks | Typical good 3 month old Cheddar | good body and texture equal to 6 month old |
| 16 weeks | Good cheese 3-4 month age | Good body and texture close and smooth, equal to 6 months old |
| 18 weeks | Good 4-5 month Cheddar | Equal to 6 month old |
| 20 weeks | Good body and texture Reasonable flavour, equal to 5 month Cheddar | Good body and texture Close and smooth waxy, 7-8 month old |
| 22 weeks | Good body and texture Reasonable flavour Equal to 5 month Cheddar | Good body and texture Close and smooth waxy 7-8 month old. |

| | GRADING AT 11 WEEKS OLD (NACPE POINTS) | |
|---|---|---|
| | VAT 9 | VAT 10 |
| Flavour | 40 | 40 |
| Body Texture | 33 | 33 |
| Colour | 9 | 10 |
| Finish | 5 | 5 |
| | 87 points | 88 points |

TABLE 3

COMPARISON OF TCA SOLUBLE AMINO ACIDS IN CONTROL AND ACCELERATED CHEESES WITH TIME

| | Nano Moles/per ml of sample | | | | | |
|---|---|---|---|---|---|---|
| TIME | 20 days Control | 20 days Accel. | 84 days Control | 89 days Accel. | 172 days Control | 172 days Accel. |
| Taurine | —* | — | — | — | — | — |
| Urea | — | — | — | — | — | — |
| Asp | 40 | 45 | 44 | 190 | 79 | 300 |
| Thre | 9.1 | 17 | 14 | 69 | 29 | 140 |
| Ser | 12 | 21 | 11 | 98 | 18 | 120 |
| Asn | — | — | — | — | — | — |
| Glu | 87 | 140 | 130 | 610 | 240 | 980 |
| Gln | — | — | — | — | — | — |
| Sarcosine | — | — | — | — | — | — |
| α-amino adipic | — | — | — | — | — | — |
| Pro | — | — | — | — | — | — |
| Gly | 11 | 22 | 14 | 105 | 31 | 170 |
| Ala | 24 | 70 | 26 | 134 | 49 | 190 |
| Citrulline | — | — | — | — | 3.9 | 37 |
| β-amino butyric | — | — | — | — | — | — |
| Val | 20 | 41 | 39 | 220 | 80 | 360 |
| Cystine | — | — | — | — | — | — |
| Met | 2.4 | 2.0 | 11 | 46 | 23 | 85 |

TABLE 3-continued

COMPARISON OF TCA SOLUBLE AMINO ACIDS IN CONTROL AND ACCELERATED CHEESES WITH TIME

| TIME | 20 days Control | 20 days Accel. | 84 days Control | 89 days Accel. | 172 days Control | 172 days Accel. |
|---|---|---|---|---|---|---|
| Cystathionine | — | — | — | — | — | — |
| Ileu | 4.2 | 15 | 8.9 | 120 | 20 | 250 |
| Leu | 55 | 78 | 94 | 370 | 190 | 530 |
| Tyr | 7.7 | 13 | 9.2 | 70 | 11 | 110 |
| Phe | 30 | 41 | 52 | 170 | 100 | 250 |
| β-amino butyric acid | — | — | — | — | — | — |
| β-alanine | — | — | — | — | — | — |
| γ-amino butyric acid | — | — | — | — | — | — |
| Ornithine | 3.5 | 0.5 | 25 | 3.1 | 58 | 63 |
| Lys | 41 | 94 | 55 | 370 | 110 | 610 |
| Tryp | — | — | — | — | — | — |
| His | 7.0 | 15 | 8.4 | 83 | 14 | 170 |
| 1-Me-His | — | — | — | — | — | — |
| 3-Me-His | — | — | — | — | — | — |
| Arg | 23 | 46 | 18 | 170 | 22 | 120 |

*not determined

TABLE 4

LOW FAT CHEDDAR CHEESE RECIPES

| | CONVENTIONAL | ACCELERATED |
|---|---|---|
| MILK | 1100 gallons | 1100 gallons |
| Fat | 1.62% these will | 1.62% these will |
| Protein | 3.20% vary | 3.20% vary |
| STARTER/S | Starter of the day but reduced by 10% of normal rate. Acidity: 1.58% LA | Starter of the day reduced by 15% of normal rate. Acidity: 1.58% LA 2 gallons of L. helveticus AGC1 culture. Acidity: 1.50% LA |
| RIPENING TEMP. | 90° F. | 90° F. |
| RIPENING TIME | 30 mins | 30 mins |
| RENNET | 43 oz | 43 oz |
| SETTING TIME | 45 mins | 45 mins |
| CUTTING SPEED | Speed 8 for 8 mins (large cut) | Speed 8 for 8 mins (large cut) |
| SCALD TEMP. | 92° F. (Acidity: 0.12% LA) Scald up in 20 mins (Acidity: 0.125% LA) | 96° F. (Acidity 0.12% LA) Scald up in 20 mins (Acidity: 0.125% LA) |
| PITCHED | 10 minutes after scald up | 10 minutes after scald up |
| WHEY OFF | 15 minutes (Acidity: 0.15% LA) | 15 minutes (Acidity: 0.16% LA) |
| ACID DEVELOPMENT (Time from Renneting) | 2 hrs 0.18% LA 2.5 hrs 0.27% LA 3 hrs 0.35% LA 3.5 hrs 0.49% LA 3 hrs 50 mins 0.57% LA | 2 hrs 10 mins 0.21% LA 2 hrs 40 mins 0.27% LA 3 hrs 20 mins 0.45% LA 3 hrs 50 mins 0.55% LA |
| MILLED | @ 0.57% LA | @ 0.55% LA |

TABLE 5

TYPICAL AGEING PROFILE FOR ACCELERATED AS COMPARED TO CONVENTIONAL LOW FAT CHEDDAR CHEESE

| AGE OF CHEESE | GRADING/COMMENTS CONVENTIONAL (NORMAL STARTER) | ACCCELERATED (NORMAL STARTER + L. HELVETICUS AGC1) |
|---|---|---|
| 3 weeks | Good body and texture Mild flavour | Good body and texture Clean, good flavour, more flavour than conventional |
| 4 weeks | Good body and texture Clean, mild flavour | Good body and texture Good, clean flavour |
| 6 weeks | Good body and texture Clean, mild flavour | Good body and texture Good, clean, well developed flavour |
| 7 weeks | Good body and texture Clean, mild flavour | Good body and texture Good, clean, mature flavour |
| 11 weeks | Good body and texture Clean flavour | Good body and texture Good, clean mature flavour |
| 18 weeks | Good body and texture Clean and slightly | Good body and texture Good mature flavour |

TABLE 5-continued

TYPICAL AGEING PROFILE FOR ACCELERATED AS COMPARED TO CONVENTIONAL LOW FAT CHEDDAR CHEESE

| | GRADING/COMMENTS | |
|---|---|---|
| AGE OF CHEESE | CONVENTIONAL (NORMAL STARTER) | ACCCELERATED (NORMAL STARTER + L. HELVETICUS AGC1) |
| | sweet | |

I claim:

1. A method of making cheddar-style cheeses which comprises:
   a. adding to milk a mixture of starter cultures which includes Lactobacillus helveticus AGC1 (NCIB 40051);
   b. permitting the milk to ripen;
   c. adding rennet to the ripened milk;
   d. permitting the resulting milk to set and form a curd;
   e. cutting the curd, stirring and heating to scald temperature;
   f. separating the curd from the whey;
   g. cheddaring the curd; and
   h. recovering the cheeses.

2. A method according to claim 1 wherein the curd from step g is milled, salted, pressed and allowed to mature.

3. A method according to claim 1, in which the cheese has a fat content of 20 to 38% and a moisture content of 30 to 45%.

4. A method according to claim 1, in which the cheese has a fat content of 8 to 20% and a moisture content of 37 to 54%.

5. A method according to claim 1, in which *Lactobacillus helveticus* AGC1 is added to a proportion of 0.05 to 0.3%, based on the total weight of the starting milk.

6. A method according to claim 1, in which the scald temperature is in the range of 94° to 108° F.

7. A method according to claim 1 wherein the starter cultures are added to the milk in a proportion of 0.01 to 1%.

* * * * *